United States Patent [19]

Knollmueller

[11] 4,077,993

[45] Mar. 7, 1978

[54] METHOD FOR THE PREPARATION OF ALKOXYSILANE CLUSTER COMPOUNDS

[75] Inventor: Karl O. Knollmueller, Hamden, Conn.

[73] Assignee: Olin Corporation, New Haven, Conn.

[21] Appl. No.: 791,358

[22] Filed: Apr. 27, 1977

[51] Int. Cl.² ............................. C07F 7/04; C07F 7/18
[52] U.S. Cl. ....................... 260/448.8 R; 260/448.8 A
[58] Field of Search .................. 260/448.8 A, 448.8 R

[56] References Cited

U.S. PATENT DOCUMENTS

| 2,566,364 | 9/1951 | Pedlow et al. ........... 260/448.8 A X |
| 2,711,418 | 6/1955 | Kather et al. ................ 260/448.8 A |
| 2,995,593 | 8/1961 | Kovacich et al. ............ 260/448.8 A |
| 3,019,191 | 1/1962 | Furby et al. ............... 260/448.8 A X |
| 3,960,913 | 6/1976 | Knollmueller ............... 260/448.8 R |
| 3,965,135 | 6/1976 | Knollmueller ................ 260/448.8 A |
| 3,965,136 | 6/1976 | Knollmueller ................ 260/448.8 A |

Primary Examiner—Paul F. Shaver
Attorney, Agent, or Firm—Robert J. Feltovic; Thomas P. O'Day; F. A. Iskander

[57] ABSTRACT

An improved method is disclosed for preparing alkoxysilane cluster compounds having the formula:

$$RSi[OSi(OR')_3]_3$$

wherein R is hydrogen, an alkyl, alkenyl, aryl or aralkyl group and each R' is independently selected from alkyl, alkenyl, aryl and aralkyl with the proviso that at least a majority of the R' radicals are sterically hindered alkyl groups having at least 3 carbon atoms. The improved preparation method involves reacting a substituted trihalosilane with a trialkoxysilanol in the presence of a critical amount of an acceptor base in a solvent reaction medium while maintaining the reactor temperature within a select range.

5 Claims, No Drawings

METHOD FOR THE PREPARATION OF ALKOXYSILANE CLUSTER COMPOUNDS

BACKGROUND OF THE INVENTION

The subject alkoxysilane cluster compounds produced by the method of the present invention are disclosed in the present inventor's U.S. Pat. No. 3,965,136. This patent describes a method for preparing these compounds by reacting a substituted trihalosilane with a trialkoxysilanol in the presence of an acceptor base, and, optionally, a solvent. The present invention defines critical limitations within such a preparation method in order to minimize competing side reactions and maximize desired product yield.

DETAILED DESCRIPTION OF THE PREFERRED EMBODIMENT

The alkoxysilane cluster compounds prepared according to the improved method of the present invention are represented by the general formula:

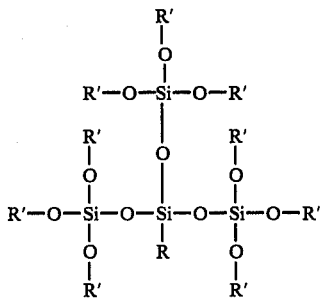

wherein R, is hydrogen, an alkyl, alkenyl, aryl or aralkyl group and each R' is independently selected from alkyl, alkenyl, aryl and aralkyl with the proviso that at least a majority of the R' radicals are sterically hindered alkyl groups having at least 3 carbon atoms.

In the present method of preparing the subject alkoxysilane cluster compounds, a trialkoxysilanol is reacted with a trihalosilane in the presence of a critical amount of an acceptor base in a solvent reaction medium within a regulated temperature range.

The trialkoxysilanol reactant is represented by the formula:

$$\text{HOSi(OR')}_3 \qquad \qquad \text{II}$$

wherein R' groups are independently selected from alkyl, alkenyl, aryl and aralkyl with the proviso that at least a majority of the R' groups are sterically hindered alkyl groups having at least 3 carbon atoms. The preferred groups for R' are alkyl or alkenyl having about 1 to about 24 carbon atoms or aryl or aralkyl having about 6 to about 24 carbon atoms. Preferably, at least a majority of the R' groups are sterically hindered alkyl groups having about 3 to about 24 carbon atoms; most preferably, all of the R' groups are sterically hindered alkyl groups having about 4 to about 12 carbon atoms. Sterically hindered alkyl groups are defined as alkyl radicals which contribute to the hydrolytic stability of the molecule, i.e., which inhibit the reaction of water with the silicon-oxygen or the carbon-oxygen bonds in the molecule. Exemplary of preferred sterically hindered alkyl radicals are non-linear primary alkyl radicals having a beta position side chain of at least 2 carbon atoms, secondary alkyl radicals and tertiary alkyl radicals. Particularly preferred groups include sec-butyl, isobutyl, 2-ethyl butyl, 2-ethyl pentyl, 3-ethyl pentyl, 2-ethyl hexyl, 3-ethyl hexyl, 2,4-dimethyl-3-pentyl, and the like.

The trihalosilane reactant used in the present invention is a substituted trihalosilane of the general formula:

$$\text{R-SiX}_3 \qquad \qquad \text{III}$$

wherein R is hydrogen, an alkyl, alkenyl, aryl or aralkyl group. Preferably, R is hydrogen, an alkyl or alkenyl having about 1 to about 18 carbon atoms or an aryl or aralkyl having about 6 to about 24 carbon atoms. Most preferably, R is hydrogen, an alkyl having about 1 to about 8 carbon atoms or an aryl or aralkyl having about 6 to about 14 carbon atoms. The X groups are halogen groups independently selected from F, Cl, Br, and I; preferably selected from Cl, Br and I. Most preferred is a trihalosilane reactant wherein X is Cl.

The acceptor base compound may be any compound which will accept hydrogen halide and thereby promote the formation of the intermediates and the cluster compounds of the present invention. Among the preferred acceptor bases are the nitrogenated tertiary organic base compounds having at least 3 carbon atoms, e.g., the lower alkyl and aryl tertiary amines such as triethyl amine, tributyl amine, as well as pyridine, substituted pyridine, N,N'-dimethylaniline and the like. Pyridine and substituted pyridines are particularly preferred.

The cluster-forming reaction is conducted in a solvent medium, in order to moderate the rate of the reaction and accommodate the post-reaction separation of the acceptor base-hydrohalide from the product. The solvent medium may be nonprotonic solvent which does not interfere with the reaction. In addition, the reactants (Formulas II and III and the acceptor base) must be soluble in the chosen solvent, and the acceptor base-hydrohalide must be insoluble in the medium to facilitate its removal from the product. Preferred solvents include benzene, toluene, xylene, hexane, heptane, high-boiling petroleum ethers, and other ethers such as tetrahydrofurane, dioxane and the like. Aromatic solvents, such as benzene and toluene are particularly preferred.

The product compounds and the reaction materials utilized in the present invented method are described further in the present inventor's U.S. Patent No. 3,965,136. The entire disclosure of this patent is hereby incorporated by reference.

The improved method for preparing the novel alkoxysilane ester clusters involves the principal reaction outlined in Equation A below between a trialkoxysilanol and a trihalosilane (Formulas II and III respectively) in the presence of an acceptor base (Z):

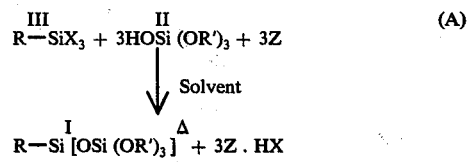

In addition to the principal reaction as set forth in Equation (A) above, several other reactions also may occur. These side reactions are set forth in detail in the present inventor's patent referred to above.

It has now been discovered that another major competing side reaction also occurs, which can be outlined as shown below in Equation (B):

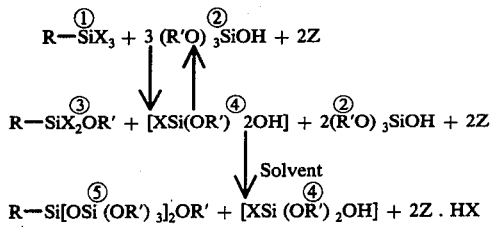

(B)

wherein Z is the acceptor base, and the other reactants are as defined above in Formulas II and III. The product, an alkoxysilane ester cluster compound, also is a useful cluster compound. This compound is further described in the present inventor's co-pending U.S. Pat. application, Ser. No. 791,359, filed concurrently herewith, which is hereby incorporated by reference in its entirety.

The initial phase of the discovered side reaction, outlined in Equation (B), is a disproportionation reaction between the trihalosilane①(Formula III) and the trialkoxysilanol ②(Formula II) to form intermediate dismutation products③and④. The dismutation product ④is unstable and has not been isolated. However, intermediate③in the presence of additional trialkoxysilanol, reacts to form the alkoxysilane ester cluster compound, shown as product⑤.

It has now been found that yields of the desired alkoxysilane cluster product of Formula I via Equation (A) can be enhanced by minimizing the effects of the unexpected competing reaction of Equation (B) by avoiding specific reactant and solvent proportions and specific reaction conditions that have been found to promote the competing reaction. In particular, it has been discovered that acceptor base levels (about stoichiometric quantities), relatively high solvent levels (about 2 to about 5 parts solvent per part total reactants by volume), and higher reaction temperatures (about 70° C to about 100° C) favor the undesired by-product ⑤formation.

In preparing the desired cluster compounds of Formula I, generally about 2.5 to about 10 moles, and, preferably, about 3.0 to about 6.0 moles of the trialkoxysilanol is used per mole of trihalosilane. Most preferably, about a stoichiometric amount of trialkoxysilanol (about 2.8-3.3 moles/mole trihalosilane) is used.

The acceptor base generally can be used in an amount ranging from about 2.5 to about 10 moles per mole of trihalosilane. However, it has now been discovered that consistently enhanced yields are obtained by using an excess of the stoichiometric amount of the acceptor base in a ratio of moles of acceptor base to moles of trihalosilane of about 3.5:1 to about 4.5:1.

The total solvent generally can vary from about 0.5 to about 10 parts of solvent per part by volume of total reactants. However, it has been discovered that using a low proportion of solvent in a ratio of about 0.8 to about 1.8 parts per part by volume of total reactants favors increased yeilds. Aromatic solvents, in particular, are favorable.

The reaction generally can be performed at a wide range of temperatures from very low temperatures, e.g., about −30° C, to very high temperatures, e.g., about 100° C, or up to the reflux temperature of the lowest boiling ingredient. To minimize loss of the volatile trihalosilane reactant, the reaction initially is carried out at low temperatures (about −10° to about 20° C) and then finished up at higher hold temperatures (about 50° to 100° C) to drive the reaction as far as possible to completion. It has now been discovered that a reaction scheme wherein an initial temperature of from about −5 to about +5° C is used for a period of about 0.5 to 2 hours during addition of reactants, followed by finishing-up the reaction at a relatively low hold temperature of about 55 to about 60° C for about 0.5 to about 12 hours, maximizes desired product yield. In practicing the reaction, a continuous operation may also be arranged whereby the first reactor in a series of reactors in maintained at the lower temperature and each subsequent reactor is incrementally higher in temperature to drive the reaction to completion.

A preferred routine in conducting the reactions to first charge the reactor vessel with the acceptor base and the trialkoxysilanol reactor dissolved in solvent. The reactor contents are then stirred and maintained within the specified temperature range while a solution of trihalosilane reactant, in solvent, is added dropwise over the specified addition period.

Both the main desired product (Formula I) and the by-product produced by the competing reaction of Equation (B) are alkoxysilane cluster compounds which are useful as functional fluids. The product mixture is first passed through a filter to remove the acceptor base-hydrohalide. Alternatively, it is preferred to waterwash the product mixture, preferably several times, to dissolve the acceptor base-hydrohalides. The lower aqueous phase readily can be phased out. Then, desiccants can be used to dry the product solution, or preferably the water can be azeotroped off with solvent. Next, the solvent can be stripped and the products can be separated by fractionation. The desired degree of product purity determines the choice and extent of product separation method.

The following examples depict preparation of the subject alkoxysilane cluster compounds using a range of reactant proportions and reaction conditions. Tables I and II summarize the examples and serve to highlight the effects of reactant proportions and reaction conditions on product yield. The examples are intended to be illustrative and not limiting in nature. All parts and percentages are by weight unless otherwise specified.

EXAMPLE I

A one liter three-neck flask is equipped with a stirrer, reflux condenser, thermometer, and equilibrated dropping funnel. Provisions are made to change quickly from a cooling bath to a heating mantle without disturbing the setup. To provent moisture from entering, the reflux condenser is topped with a $CaCl_2$ tube, while a slow stream of dry nitrogen is passed through the apparatus via the equilibrated funnel. The flask is charged with 132.2 g of a trialkoxysilanol, having the formula $HOSi(OC_4H_9 \text{ sec})_3$(0.5 moles), 63.3 g pyridine (0.8 moles) as the acceptor base, and 300 ml toluene. A solution of 24.91 g of a trihalosilane of the formula $H_3CSiCl_3$ (0.166 moles) in 50 ml toluene is placed into the dropping funnel. The flask contents are set at an initial temperature of 0° C and the trihalosilane solution is added dropwise, with stirring, at such a rate as to maintain the initial temperature between 0° and +5° C. After the addition is completed (about 1 hour), the contents of the flask are stirred without cooling for 30 minutes, then rapidly warmed up and maintained for 4 hours at a hold temperature of 60° C. The contents are then allowed to cool to room temperature while standing overnight.

To the cooled reaction mixture is added 100 ml water and the contents are stirred for 5 minutes. The pyridine hydrochloride is dissolved in the aqueous phase together with some of the excess pyridine present. The phases are allowed to separate; the lower aqueous phase is syphoned off. This wash is repeated twice to hydrolyze any remaining Si-Cl bonds and take out residual pyridine hydrochloride. The reflux condenser is now placed on top of a Dean Stark Trap which is attached to the flask. The organic phase is now refluxed and the residual water removed in the trap. During this operation any milky appearance of the organic phase, due to finely dispersed water droplets, clears rapidly and after about a 30–45 minute azeotroping, a clear organic phase is obtained. Most of the solvent is now removed through the Dean Stark Trap by distillation. The residual solution is vacuum stripped from the remainder of the solvent, giving about 138 g crude product. Analysis of the crude product by vapor phase chromatography (VPC) reveals 3.86% by weight high boiler, 64.9% by weight of the desired product alkoxysilane cluster of the formula $CH_3Si[OSi(OC_4H_9sec)_3]_3$, 10.6% by weight of a by-product alkoxysilane ester of the formula $CH_3Si[OSi(OC_4H_9 sec)_3]_2OC_4H_9$ sec. The residuals are about 9.8% by weight silanol of the formula $CH_3Si[OSi(OC_4H_9sec)_3]_2OH$ and the residual 11.7% by weight are distributed among small amounts of unreacted silanol, orthosilicate, and disiloxane.

When the mixture is fractionated on a micro Vigreux column, the lower boiling components including the silanol $CH_3Si[OSi(OC_4H_9)_3]_2OH$ are distilled off, boiling from ~80° C to 150° C/0.05 mm, totalling 28 g.

In the next fraction, boiling at 161–65/0.05 mm, the by-product ester $CH_3Si[OC_4H_9 sec)_3]_2OC_4H_9$ sec is obtained in an amount of 14.2 g. Finally, in the last fraction, the desired cluster compound of the formula $CH_3Si[OC_4H_9 sec)_3]_3$ is obtained at 192°/0.05 mm in an amount of 84 g.

Based on methyltrichlorosilane charged and VPC data, the yields in the products of interest are:

Formula I Alkoxysilane Cluster $H_3CSi[OSi(OC_4H_9)_3]_3$ 64.11%

By-Product Alkoxysilane Ester
$CH_3Si[OSi(OC_4H_9)_3]_2OC_4H_9$ 10.6% of theory

In-hand yields after distillation are generally somewhat lower due to incomplete separations, transition cuts or small rates of decomposition.

The in-hand yields of the desired cluster silicate is 60.9% of theory, by-product ester silicate 10.3% of theory.

Characterization of the ester by-product $CH_3Si[OSi(OC_4H_9)_3]_2OC_4H_9$ is done by mass spectroscopy and verified by elemental analysis of a more purified sample.

Calculated for $C_{29}H_{66}O_9Si_3$:
  Theoretical: C = 54.16%; H = 10.35%; Si = 13.10%
  Actual—: C = 54.31%, 54.21%; H = 10.25%, 10.14%; Si = 12.92%

EXAMPLES II - IX

In the following table the abbreviations $H_3CSi[Y]_3$ is used for the desired alkoxysilane cluster product $H_3CSi[OSi(OC_4H_9 sec)_3]_3$ and $H_3CSi[Y]_2OR$ is used for the alkoxysilane ester by-product $H_3CSi[OC_4H_9 sec)_3]_2OC_4H_9$.

In all of the examples II-IX, the procedure of Example I is used, and in each case 132.2 g (0.5 mole) silanol $HOSi(OC_4H_9)_3$ is reacted with 24.91 g methyltrichlorosilane $CH_3SiCl_3$ (0.166 mole). The variations in pyridine and toluene solvent level, hold Temperatures, and yields, based on $CH_3SiCl_3$ and VPC data are recorded in Table I. (Examples I and X* data is included.)
* Preparation method (see below) uses a ratio of reactants $CH_3SiCl_3$/silanol of 1:3.22 (Examples I–IX and XI–XIX use a 1:3 ratio).

EXAMPLE X

Preparation of Cluster Silicate in Toluene

The general procedure of Example I is repeated using a 5 liter flask as reactor, a solution of 1143 g silanol of the formula $HOSi(OC_4H_9)_3$ 93.7% purity by VPC = 4.325 moles and 426 g pyridine 5.39 moles (a 33% excess) in 1200 ml toluene is reacted at 5° C with a solution of 202 g $CH_3SiCl_3$ (1.351 moles) in 400 ml toluene, within two hours. The temperature is raised to 55° C and held there for 12 hours. After work-up, involving four washes with 700 ml water each, azeotroping and vacuum stripping one obtains 1062 g of a product, containing 74.6% by weight of the desired cluster $CH_3Si[Y]_3$, as well as 8.2% by weight $CH_3Si[Y]_2OR$.

| $CH_3Si[Y]_3$ | 70.36% |
| $CH_3Si[Y]_2OR$ | 10.02% |

The in-hand yield of pure $CH_3Si[Y]_3$ after distillation is 65% and $CH_3Si[Y]_2OR$ is 9.5%.

TABLE I

| Example No. | Pyridine g | Pyridine/$CH_3SiCl_3$ molar ratio | Toluene ml | Solvent/Silanol volume ratio | Hold Temp.° C | Yields based on $CH_3SiCl_3$% charged | |
|---|---|---|---|---|---|---|---|
| | | | | | | $CH_3Si[Y]_3$ | $CH_3Si[Y]_2OR$ |
| I | 63.3 | 4.82:1 | 300 | 2.06:1 | 60 | 64.11 | 10.6 |
| II | 95 | 7.22:1 | 130 | 0.89:1 | 40 | 74.3 | 8.0 |
| III | 95 | 7.22:1 | 130 | 0.89:1 | 90 | 67 | 15.3 |
| IV | 39.6 | 3:1 | 600 | 4.12:1 | 40 | 53 | 14.2 |
| V | 39.6 | 3:1 | 600 | 4.12:1 | 90 | 34.2 | 49.8 |
| VI | 95 | 7.22:1 | 600 | 4.12:1 | 90 | 60.1 | 24.9 |
| VII | 95 | 7.22:1 | 600 | 4.12:1 | 40 | 70.2 | 7.1 |
| VIII | 39.6 | 3:1 | 130 | 0.89:1 | 90 | 57.7 | 28.0 |
| IX | 39.6 | 3:1 | 130 | 0.89:1 | 40 | 65.2 | 10.1 |
| X | 426.0 | 3.99:1 | 1200 | 0.89:1 | 55 | 70.36 | 10.02 |

EXAMPLES XI - XIX

The reaction conditions of Examples XI–XIX are the same as Examples I–X, but n-heptane rather than toluene is the solvent medium used. The procedure of Example I is repeated in each case. Table II shows the results.

TABLE II

| Example No. | Pyridine g | Pyridine/CH$_3$SiCl$_3$ molar ratio | n-Heptane ml | Solvent/Silanol Volume ratio | Hold Temp.° C | Yields (VPC) based on CH$_3$SiCl$_3$ charged | |
|---|---|---|---|---|---|---|---|
| | | | | | | CH$_3$Si[Y]$_3$ | CH$_3$Si[Y]$_2$OR |
| XI | 63.3 | 4.82:1 | 350 | 2.06:1 | 60 | 48.9 | 11 |
| XII | 95 | 7.22:1 | 130 | 0.89:1 | 40 | 60.2 | 11.5 |
| XIII | 95 | 7.22:1 | 130 | 0.89:1 | 90 | 67.3 | 14.1 |
| XIV | 39.6 | 3:1 | 600 | 4.12:1 | 40 | 35.9 | 20.8 |
| XV | 39.6 | 3:1 | 600 | 4.12:1 | 90 | 39.3 | 26.6 |
| XVI | 95 | 7.22:1 | 600 | 4.12:1 | 90 | 53.4 | 23.8 |
| XVII | 95 | 7.22:1 | 600 | 4.12:1 | 40 | 51.4 | 14.5 |
| XVIII | 39.6 | 3:1 | 130 | 0.89:1 | 90 | 53.1 | 23.7 |
| IX | 39.6 | 3:1 | 130 | 0.89:1 | 40 | 45 | 20.3 |

I claim:

1. In a method for preparing an alkoxysilane cluster compound of the formula:

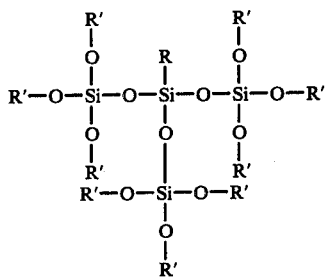

wherein R is hydrogen, alkyl, alkenyl, aryl or aralkyl, and each R' is independently selected from alkyl, alkenyl, aryl or aralkyl with the proviso that at least a majority of R' radicals are sterically hindered alkyl groups having at least 3 carbons atoms,
comprising reacting a trihalosilane of the formula:

R—SiX$_3$ wherein each X is a halogen and R is as defined above, with a trialkoxysilanol of the formula:

HOSi(OR')$_3$ wherein R' is as defined above, in the presence of an acceptor base compound, an improvement characterized by reacting about 2.8 to about 3.3 moles of trialkoxysilanol per mole of the trihalosilane in the presence of about 3.5 to about 4.5 moles of acceptor base per mole of trihalosilane, in a non-protonic solvent medium comprising about 0.8 to about 1.8 parts solvent per part total reactants by volume, said reaction being carried out at a temperature of about −5° C to about 60° C.

2. The improved method of claim 1 wherein the acceptor base compound is selected from the group consisting of pyridine and substituted pyridines.

3. The improved method of claim 2 wherein the non-protonic solvent is an aromatic solvent.

4. The improved method of claim 3 wherein the aromatic solvent is toluene.

5. The improved method of claim 3 wherein said reaction is carried out at an initial temperature of about −5° C to about +5° C during addition of reactants, followed by a reaction hold period of about 0.5 to about 12 hours at about 55° C to about 60° C.

* * * * *